US00PP25061P3

(12) United States Plant Patent
Korlipara

(10) Patent No.: US PP25,061 P3
(45) Date of Patent: Nov. 11, 2014

(54) *ECHINACEA* PLANT NAMED 'SECRET GLOW'

(50) Latin Name: ***Echinacea* spp.**
Varietal Denomination: Secret Glow

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 231 days.

(21) Appl. No.: 13/694,351

(22) Filed: Nov. 21, 2012

(65) Prior Publication Data

US 2014/0143923 P1 May 22, 2014

(51) Int. Cl.
*A01H 5/00* (2006.01)

(52) U.S. Cl.
USPC ..... Plt./428

(58) Field of Classification Search
CPC ..... A01H 5/025; A01H 5/00; A01H 5/02
USPC ..... Plt./428
See application file for complete search history.

*Primary Examiner* — June Hwu
(74) *Attorney, Agent, or Firm* — Klarquist Sparkman, LLP

(57) ABSTRACT

A new and distinct *Echinacea* plant named 'Secret Glow' characterized by enlarged disc florets forming an anemone-type inflorescence, yellow orange ray florets and light orange disc florets, a medium sized, mounding habit with excellent stem count and good branching, and excellent vigor

1 Drawing Sheet

Botanical denomination: *Echinacea* spp.
Variety designation: 'Secret Glow'.

BACKGROUND OF THE INVENTION

The present invention relates to a new and distinct cultivar of *Echinacea* and given the cultivar name 'Secret Glow'. *Echinacea* is in the family Asteraceae. This new cultivar is part of a planned breeding program to create a compact double flowering series. The exact parents of this selection are unknown, unnamed, proprietary interspecific hybrids of *Echinacea paradoxa*×*Echinacea purpurea*. This cultivar was selected for its excellent flower number, color, and habit.

Compared to *Echinacea* 'Marmalade' (U.S. Plant Pat. No. 22,602), the new cultivar has inflorescences that are yellow orange changing to yellow rather than orange maturing to tan. The new cultivar has a shorter habit, better branching, more inflorescences per stem, and the inflorescences are smaller with shorter and tighter disc florets.

Compared to *Echinacea* 'Secret Joy' (U.S. Plant Pat. No 23,627), the new cultivar has deep yellow orange flowers rather than light yellow.

Compared to *Echinacea* 'Pineapple Sundae', the new cultivar has florets that are deep yellow orange rather than yellow.

This new *Echinacea* cultivar is distinguished by:

1. enlarged disc florets forming an anemone-type inflorescence,
2. yellow orange ray florets and light orange disc florets,
3. a medium sized, mounding habit with excellent stem count and branching, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows the inflorescences of *Echinacea* 'Secret Glow' on a one-year-old plant growing in the field in full sun in early September in Canby, Oreg.

DETAILED PLANT DESCRIPTION

The following is a detailed description of the new *Echinacea* cultivar based on observations of 10-month-old specimens growing in the trial bed in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, $5^{th}$ edition.

Plant:

*Type.*—Herbaceous perennial.
*Hardiness.*—USDA Zones 4 to 9.
*Size.*—Grows to about 60 cm wide and 63 cm tall to top of inflorescences.
*Form.*—Basal clump, with 7 to 20 stems from the base.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 1 to 3 inflorescences per stem.

*Size.*—To 56 cm tall to a terminal inflorescence and 4 mm wide at base.

*Internode length.*—2.5 cm to 9.5 cm.

*Surface texture.*—Strigose.

*Color.*—Yellow Green 146C.

Leaf (basal):

*Type.*—Simple.

*Shape.*—Lanceolate.

*Arrangement.*—Basal.

*Blade size.*—Grows to 12 cm long and 4 cm wide.

*Margins.*—Entire.

*Apex.*—Acute.

*Base.*—Attenuate.

*Surface texture.*—Strigose on both sides.

*Venation.*—Pinnate, with 3 main veins.

*Color.*—Topside Green N137A bottom side closest to Yellow Green 147B.

*Petiole description.*—Grows to 9 cm long and 3 mm wide, strigose, Yellow Green 146B.

Leaf (stem):

*Type.*—Simple.

*Shape.*—Lanceolate.

*Arrangement.*—Alternate.

*Blade size.*—Grows to 16 cm long and 5 cm wide.

*Margins.*—Entire.

*Apex.*—Acuminate.

*Base.*—Attenuate.

*Surface texture.*—Strigose on both sides.

*Venation.*—Pinnate, with 3 main veins from the base.

*Color.*—Topside Yellow Green N137A, bottom side closest to Yellow Green 147B.

*Petiole description.*—On all but upper leaves, clasping, grows to 12 cm long and 3 mm wide above the clasp, sparsely strigose, Yellow Green 146B.

Inflorescence:

*Type.*—Composite on terminal stalked heads.

*Number of flowering stems from the ground.*—7 to 20.

*Flowering stem.*—Grows to 58 cm tall from the base of the plant to the terminal inflorescence and can grow to 12 cm to 17 cm long from the top stem leaf to the base of an inflorescence; branched with 1 to 3 inflorescences per stem; diameter growing to 7 mm wide near the inflorescence; strigose; Yellow Green 146C.

*Size.*—Grows to 8 cm wide and 7.5 cm deep as disc enlarges.

*Form.*—Ray florets held slightly reflexed, mature disc is conic.

*Immature inflorescence.*—Grows to 2.5 cm wide and 1.7 cm deep, ray florets held at a 70 degree angle from the vertical and rolled up so only the back color shows, Yellow Orange 20C, disc color Yellow Green 144A.

*Ray florets.*—Without pistil or stamen, about 15 in number, grow to 45 mm long and 8 mm wide, oblanceolate with the tip three-toothed (each acute), entire margins, base attenuate, glabrous on both sides; topside Yellow Orange 23A, when old Yellow 13A, bottom side Yellow Orange 16D.

*Disc.*—Flat becoming conic, growing to 40 mm deep and 65 mm wide with maturity, Orange 24A.

*Disc florets.*—About 370 in number, each with 1 pistil and 4 stamen, grow to 25 mm long and 7 mm wide, each with one persistent, very stiff linear bract (14 mm long with the top 4 mm colored Yellow Orange 23A on tip then Yellow Green 144A in middle, then Yellow Green 145D on bottom ⅓); corollas 23 mm long and 7 mm wide, tubular at base (145C) then 3 main lobes, the center lobe grows to 17 mm long and 4 mm wide and has 3 terminal lobes, the two side lobes linear 15 mm long and 1.5 mm wide, all lobes glabrous, margins entire, tips acuminate, topside Orange 24A, bottom side Yellow Orange 16D; pistil 10 mm long, ovary 4 mm long, White 155A, style 6 mm long Yellow Green 145D, 2-branched stigma spreading, Grey Brown 199B; stamen 4 mm long, filaments 4 mm long, threadlike, Yellow Green 145D, anthers reduced, pollen none.

*Phyllaries.*—In 4 leafy series, area grows to 31 mm wide and 8 mm deep, lobes lanceolate in shape, reflexed, grow to 10 mm long and 3 mm wide, Green 137A, margins strigose, tip acute, strigose on both sides.

*Receptacle.*—Grows to 10 mm wide and 20 mm deep, White NN155B.

*Bloom period.*—July through October in Canby, Oreg.

*Fragrance.*—Light, floral.

*Lastingness.*—Each inflorescence lasts about two weeks in Canby, Oreg.

*Seeds.*—Not seen.

*Fertility.*—Poor.

Disease and pests: No pests or diseases have been observed on plants grown under commercial conditions in Canby, Oreg. No resistances are known.

I claim:

1. A new and distinct *Echinacea* plant as herein illustrated and described.

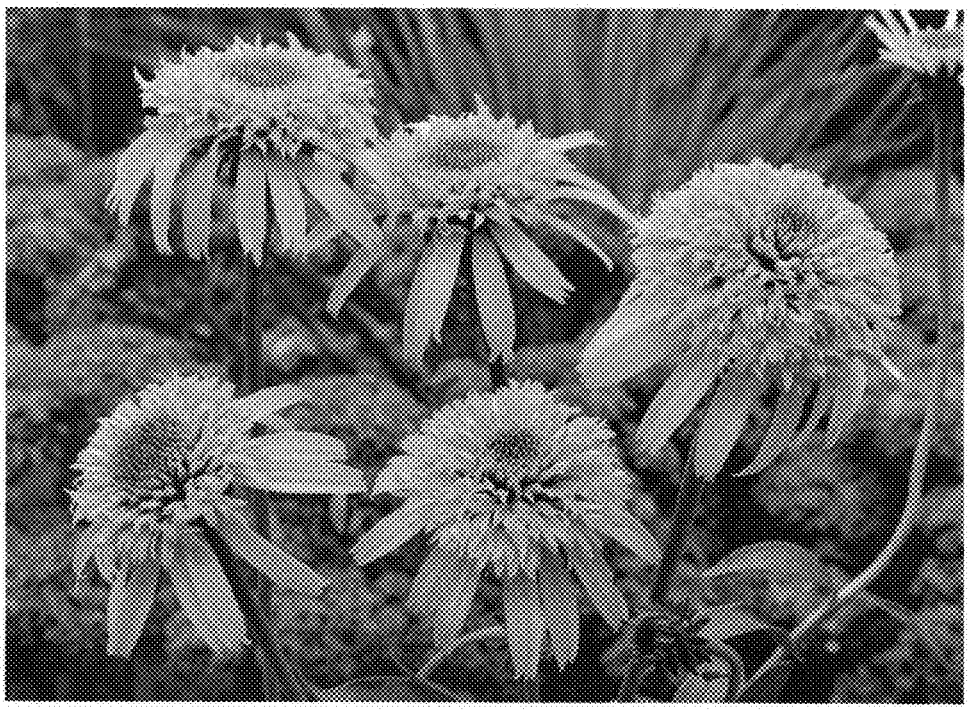

* * * * *